United States Patent [19]
Tanaka et al.

[11] Patent Number: 5,304,711
[45] Date of Patent: Apr. 19, 1994

[54] MEDICAL WASTE DISPOSAL APPARATUS

[75] Inventors: Masaya Tanaka; Koichi Murata, both of Tokyo; Mitsuru Ikeda, Kyoto; Kiyoyuki Ikuma, Kyoto; Kazuaki Jotake, Kyoto, all of Japan

[73] Assignees: Fuji Medical Systems Co., Ltd., Tokyo; Imsec Corporation, Kyoto, both of Japan

[21] Appl. No.: 889,430

[22] Filed: May 28, 1992

[30] Foreign Application Priority Data

May 29, 1991 [JP] Japan .................. 3-152265

[51] Int. Cl.⁵ ............................. B09B 3/00
[52] U.S. Cl. .................... 588/258; 210/177; 588/226
[58] Field of Search ............ 405/128, 129; 588/226, 588/249, 258; 110/203, 215; 210/175, 177, 180, 188

[56]  References Cited
U.S. PATENT DOCUMENTS

| | | |
|---|---|---|
| 4,217,222 | 8/1980 | Harendza-Harinxma . |
| 4,438,706 | 3/1984 | Boday et al. ............... 588/226 X |
| 4,919,569 | 4/1990 | Wittenzelliner ............. 405/128 |
| 4,993,873 | 2/1991 | Tippmer ..................... 405/128 |

FOREIGN PATENT DOCUMENTS

| | | |
|---|---|---|
| 3841076 | 6/1990 | Fed. Rep. of Germany ...... 588/226 |
| 3938546 | 7/1990 | Fed. Rep. of Germany ...... 588/226 |
| 1-236883 | 9/1989 | Japan . |
| 2-281756 | 10/1990 | Japan . |

Primary Examiner—David H. Corbin
Attorney, Agent, or Firm—Sughrue, Mion, Zinn, Macpeak & Seas

[57] ABSTRACT

A medical waste disposal apparatus for heating waste includes a hydrodynamic exhaust scrubber in which water is sprinkled in an atomized or spouted state into a circulation passage as the gaseous pyrolytic product and the steam flow through the passage, so that the product and the steam are dissolved in the water. The product and the steam are thus collected and removed.

12 Claims, 4 Drawing Sheets

MEDICAL WASTE DISPOSAL APPARATUS

BACKGROUND OF THE INVENTION

The present invention relates to a medical waste disposal apparatus for the safe and efficient disposal of contagious medical waste including used plastic syringes and injection needles.

The number of different kinds of waste is increasing with the diversification of industry. Some types of waste can be relatively easily disposed of by simple burning or heating, while others, such as infectious medical waste, cannot. As infectious medical waste is burned or heated, an environmentally or hygienically harmful gaseous pyrolytic product is generated. Contagious medical waste may include used plastic syringes, injection needles, or surgical operation gloves. Since these types of medical waste are typically infectious, they cannot simply be thrown away. For that reason, the waste is recovered in a prescribed container, and later placed in a bag or the like. The waste may be shredded by a shredder, if necessary, before being placed in the bag or the like. The waste can subsequently be disposed of by burning in an incinerator, sterilization by high-pressure steam, or heating. The combustion gases resulting from burning the waste can be partially removed by an appropriate dust collector. However, there are disadvantages in that the soot of the burned waste cannot be completely eliminated. Furthermore, it is necessary to employ large equipment, which is expensive to purchase, operate, and maintain. When the waste is sterilized, it may, for example, be heated to a temperature of 126° C. to 131° C. Since these temperatures are relatively low, the waste is only slightly pyrolyzed, and it is not necessary to provide means for disposing of a gas, smell or the like resulting from the sterilization. However, since the temperature is relatively low, some waste will not be sterilized. To heat the waste, an apparatus including an appropriate melting container, in which the waste is heated at a temperature of approximately 200° C. by a heating furnace, is provided. One example of such waste containers for processing is disclosed in Japanese Patent Application 281756/90. These apparatus typically exhibit good sterilization characteristics, have a simple structure, are not too large and are easy to maintain and operate. Furthermore, since heating furnaces, such as electric furnaces, are hermetically closed throughout the heating process, a pyrolytic product will not be expelled into the surrounding air. Therefore, the heating of medical waste is a very effective procedure from an environmental standpoint.

If a hospital syringe or the like, made mainly of polypropylene, is heated at a temperature of 200° C. for sterilization by the above-mentioned heating apparatus, a large quantity of pyrolytic products such as tar, acetic acid and acetaldehyde are generated from the heated material, usually at a temperature of between 170° C. and 180° C. The processed waste is ordinarily not removed from the incinerator until the incinerator has cooled adequately. Nonetheless, if tar and a gaseous pyrolytic product, such as acetaldehyde, acetic acid or acetone, are generated during the heating process and remain in the incinerator thereafter, the gaseous pyrolytic product may escape from the incinerator when the waste is removed. Furthermore, if the plastic syringe, having a melting point around 170° C., and an instrument made of polyvinyl chloride, having a much lower melting point than the syringe, are melted simultaneously by the apparatus or the incinerator described above, a harmful gas including hydrogen chloride may be generated, a gas which will likely escape from the apparatus or the incinerator at the time of removal of the processed waste. Furthermore, used syringes and the like typically contain a lot of moisture due to remaining blood or other liquid contents. The moisture becomes steam in the heating apparatus or the incinerator and fills the interior thereof during processing. The generated steam is likely to adhere to the cooled parts of the apparatus or the incinerator, at the time of cooling, after processing, and will cohere as water drops which remain in the apparatus or the incinerator for long periods of time, potentially resulting in short circuiting of the electric wirings of the incinerator.

SUMMARY OF THE INVENTION

The present invention was made in order to solve the above-mentioned problems. Accordingly, one object of the invention is to provide a medical waste disposal apparatus capable of effectively collecting and removing gaseous pyrolytic products, including steam, which are generated during the incineration or heating of infectious medical waste or the like.

The present invention is to be used for heating medical waste so as to sterilize it. The apparatus has a heater body for heating and thereby heating the waste, and a hydrodynamic exhaust scrubber having a water sprinkler for sprinkling water in an atomized or spouted state. The scrubber is able to recover the water after the sprinkling process. The heater body and water sprinkler are connected to each other through forward and backward passages including a gas drive structure. As the gaseous pyrolytic product and steam are circulated through the passages by the above-mentioned gas drive structure, harmful products are dissolved in the water, the steam is cooled by the water, and the harmful products and steam are collected and removed.

The water sprinkler includes a water sprinkling member having sprinkling nozzles in a circumferential portion, the sprinkling member extending into a space in the forward passage. The sprinkler may also include a filter in a water sprinkling area in the forward passage, the sprinkled water being directed against the filter, the gaseous pyrolytic product and steam passing through the filter. An inlet port of the water drain pipe is opened toward the bottom of the accumulated water.

In the inventive medical waste disposal apparatus, the gaseous pyrolytic product and steam are directed into a hydrodynamic exhaust scrubber disposed separately from the heater body such that the product and steam mix with the sprinkled water in an atomized or spouted state. As a result, the gaseous pyrolytic product is cooled by the water and dissolved therein, and the steam is cooled by the water and coheres as water droplets, the accumulated water then being easily recovered for further processing. A gas, devoid of the product and steam, is sent back to the heater body such that the various gases generated in the heater during the heating of the waste can be effectively removed.

DESCRIPTION OF THE PREFERRED EMBODIMENTS

Figure 1:
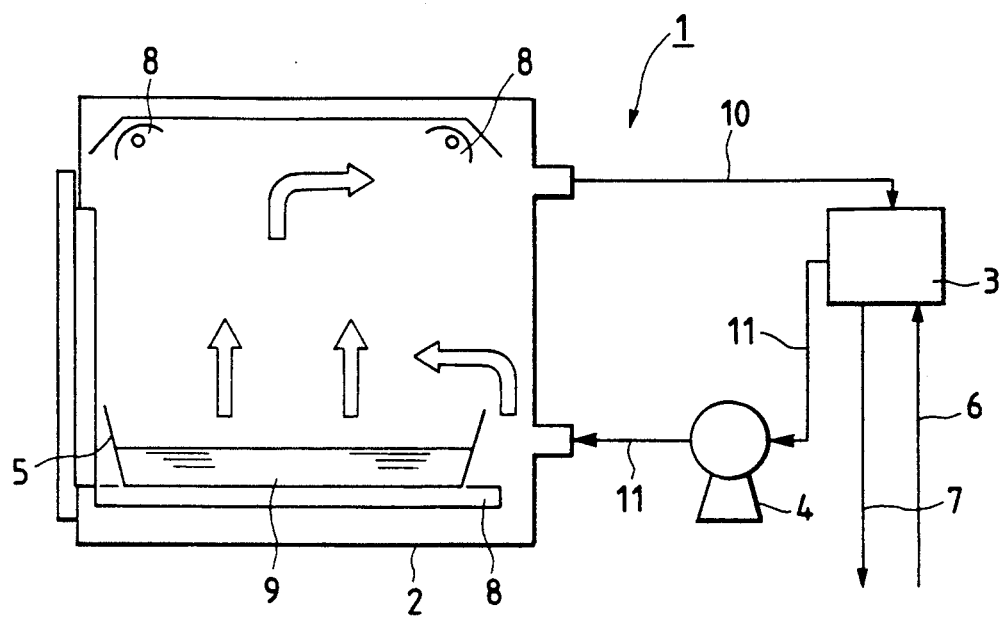
FIG. 1 is a schematic view of an embodiment of a medical waste disposal apparatus of the present invention.
Figure 2:
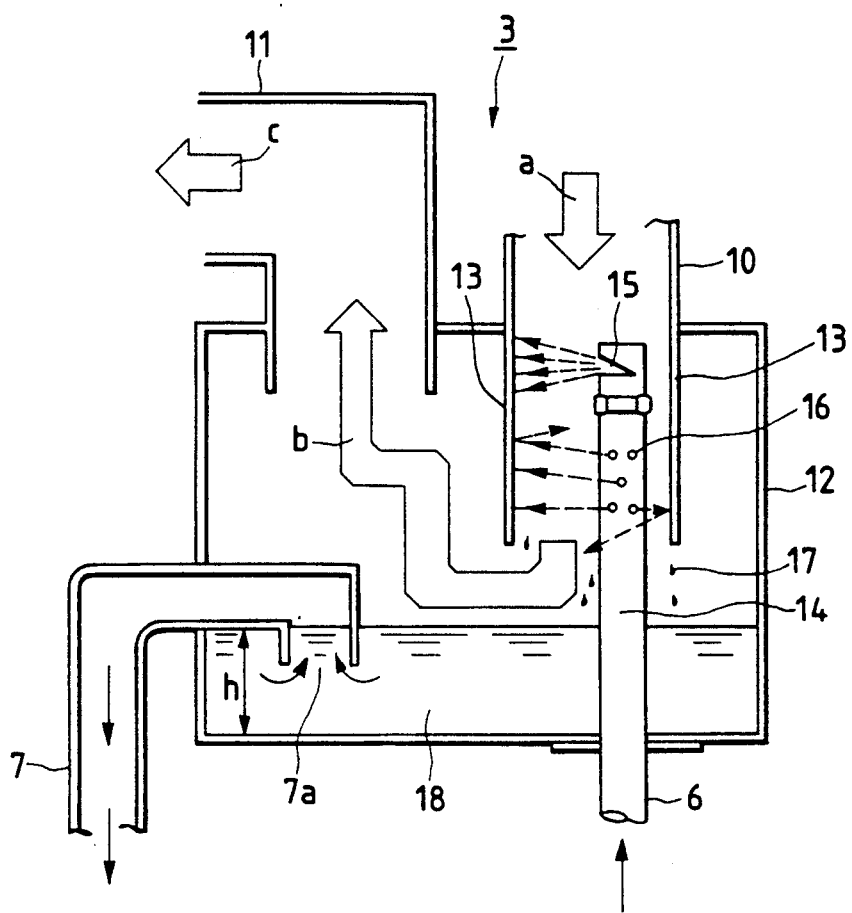
FIG. 2 is a schematic view of a hydrodynamic exhaust scrubber of the present invention.
Figure 3:
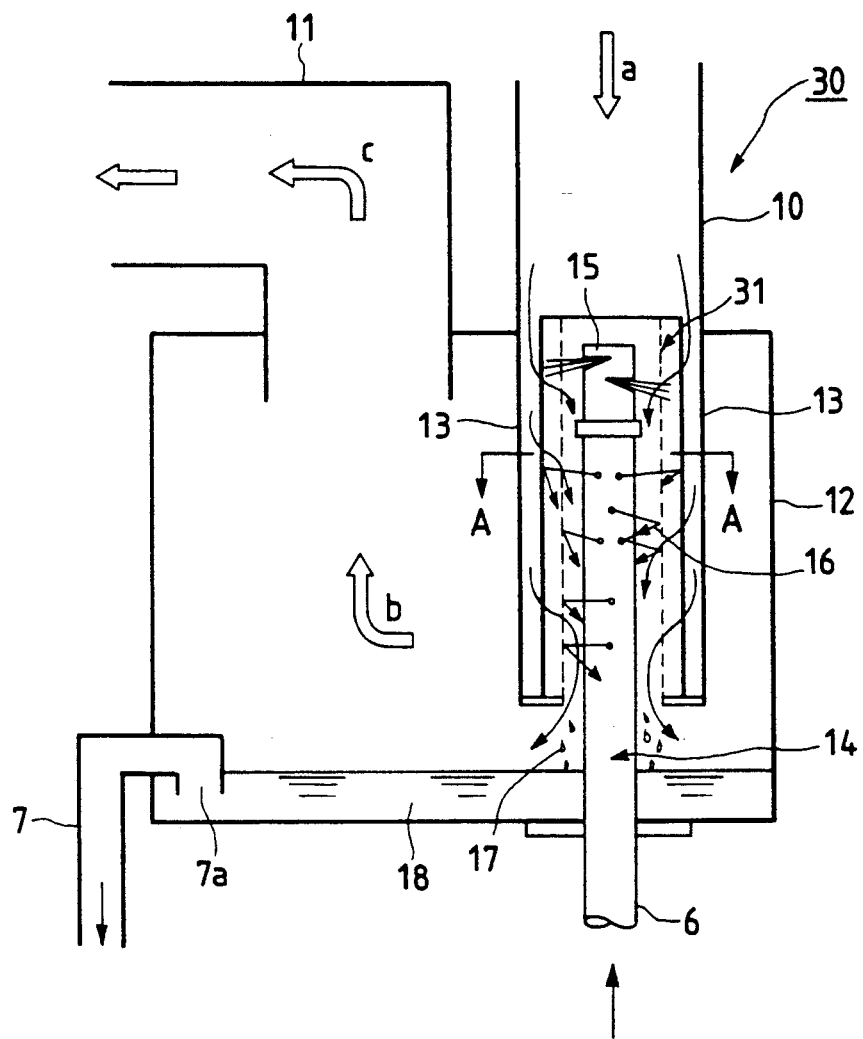
FIG. 3 is a schematic view of one modified hydrodynamic exhaust scrubber of the embodiment shown in FIG. 2.

An embodiment of the present invention is described hereafter with reference to FIGS. 1 and 2. FIG. 1 is a schematic view of an embodiment of the medical waste disposal apparatus. FIG. 2 is a schematic view of hydrodynamic exhaust scrubber of the embodiment shown in FIG. 1. The scrubber is for collecting and removing a gaseous pyrolytic product and steam.

Waste matter to be disposed of by the apparatus, such as a used plastic syringe, and the gaseous pyrolytic product generated during the disposal, are described hereafter, prior to a detailed description of the construction and operation of the apparatus shown in FIGS. 1 and 2. The plastic syringe is melted and sterilized by the apparatus while being heated at a temperature of, for example, 180° C. to 200° C. At that time, tar and gaseous pyrolytic products are generated from the molten material, and moisture remaining in the syringe is evaporated. The gaseous pyrolytic product may be, for example, formaldehyde, acetic acid, acetaldehyde, hydrogen chloride or an organic substance of low molecular weight. Although the pyrolytic product fills the interior of the body of the heater of the apparatus, the apparatus collects and removes the product during the melting of the syringe to thereby prevent leakage and, consequently, reduce the chance for environmental harm.

Formaldehyde (HCHO) and acetaldehyde ($CH_3CHO$) each reacts chemically with water to make a hydrophilic acid as, for example, formic acid (HCOOH) and acetic acid ($CH_3COOH$). Acetic acid and hydrogen chloride dissolve easily in water. The apparatus utilizes the above described properties by passing the pyrolytic product through a region of atomized water so as to cool and dissolve the product. The resulting acidic, aqueous solution is ultimately removed from the apparatus. The gaseous pyrolytic product is thus collected and removed. Solid particles of the tar and/or other organic substances of low molecular weight are similarly adsorbed by the water such that the particles are collected and removed. The steam is also directed through the atomized water and is thereby converted into cooled water, and ultimately collected and removed. Thus, the tar, gaseous pyrolytic product and steam generated from the plastic syringe during the heating thereof, are collected and removed so as to minimize environmental harm.

The collection and removal of the pyrolytic products and steam are described in detail hereafter. The apparatus 1 (FIG. 1) includes a heating section in which the used plastic syringe 9 is placed as waste in a container 5 residing inside the body 2 of the heater; a gas processing section in which the tar, the gaseous pyrolytic product, and the steam are processed by the hydrodynamic exhaust scrubber 3; and a circulation fan 4, intake pipe 10, and exhaust pipe 11, for connecting the heating and gas processing sections. Both sections are connected through the pipes 10 and 11 so that the tar, gaseous pyrolytic product and steam are introduced into the gas processing section from the heating section through a forward passage including the intake pipe 10, and the gas, removed of the tar, gaseous pyrolytic product and steam by the gas processing section, is sent back to the heating section from the gas processing section through a backward passage including the exhaust pipe 11.

The scrubber 3 includes a water sprinkler for collecting and removing the tar, product and steam generated from the waste (e.g., a syringe 9) as the waste is heated by the heater. As shown in FIG. 2, the intake pipe 10 and the exhaust pipe 11 are connected to the appropriate portions of the case 12 of the scrubber 3. The water sprinkler has a water sprinkling member 14 for sprinkling the water in an atomized or spouted state inside a partition wall 13 defining an intake space. A water feed pipe 6, such as a water pipe connected to a public water source, is connected to the water sprinkling member 14. A water drain pipe 7 is connected to the bottom of the case 12 to drain the recovered water used for the collection and removal of the tar, product and steam. The water inlet port 7a of the drain pipe 7 is directed downwardly and is, at all times, located below the level of the accumulated water 18 in the case 12. The highest portion of the water drain pipe 7 is located at a prescribed height "h" from the bottom of the inner surface of the bottom plate of the case 12, the case 12 thus serving as a water holding vessel to store the accumulated water 18. If the level of the accumulated water 18 rises above the prescribed height "h", the water is removed from the case 12 through the drain pipe 7.

The circulation fan 4 (FIG. 1) operates such that the gas, containing the tar, gaseous pyrolytic product and steam, is sucked into the scrubber 3, the gas being cleaned by removing the tar, product and steam, the gas then being returned to the body 2 of the heater.

The water sprinkling member 14 has a water sprinkling, slit-like nozzle 15 provided in the upper end portion of the member 14 such that a portion of the water, supplied under a prescribed pressure, through the water feed pipe 6, is sprinkled out of the nozzle 15 toward a partition wall 13 defining the intake space. The sprinkling member 14 also includes a water sprinkling nozzle 16 created by a plurality of holes in the circumferential portion of the member, water being sprinkled out of the nozzle means 16 toward the partition wall 13. As a result, the high-temperature gas, containing the tar, gaseous pyrolytic product and steam, generated in the body 2 of the heater, contacts the sprinkled and atomized water in the intake space as the gas is sucked through the intake pipe 10 by the action of the circulation fan 4, in the direction shown by arrow "a" in FIG. 2. The gas enters into the case 12 of the scrubber 3, in a direction shown by the arrow "a", passes through the intake space, and flows in a direction shown by arrow "b" in FIG. 2. At that time, the high-temperature gas is cooled by the water, the tar and gaseous pyrolytic product contained in the gas are adsorbed by or dissolved in the water, and any remaining steam is converted into cooled water. An aqueous solution 17 containing the tar, pyrolytic product and water drops down into the bottom portion of the case 12 creating a body of accumulated water 18. When the accumulated water 18 exceeds a prescribed amount, the excess water is drained out of the gas processing section of the apparatus through a drain pipe 7. Since the water inlet port 7a of the drain pipe 7 is always located below the level of the accumulated water 18 in the bottom portion of the case 12, the gas, removed of the tar, gaseous pyrolytic product and steam, cannot exit with the drained water through the drain pipe. In other words, a completely closed system is formed for the gas. Thus, the tar, pyrolytic product and steam are dissolved in, or adsorbed by, the atomized water sprinkled into the intake space, such that the tar, product and steam are collected and removed from the gas. The remaining gas, having escaped from the intake space in the direction shown by arrow "b" in FIG. 2, is a clean gas which the circulation fan 4 sucks in a direction shown by arrow "c" in FIG. 2, the clean gas being returned to the heater body 2.

As described above, the medical waste disposal apparatus operates such that the tar, gaseous pyrolytic product and steam, all of which are generated during the heating of the waste, are dissolved in, or adsorbed by, the sprinkled water to thereby create an aqueous solution 18, and the tar, product and steam are effectively removed without producing foul smells and without contaminating the surrounding environment during the disposal process.

In contrast to the inventive apparatus, a conventional waste disposal apparatus, without a hydrodynamic exhaust scrubber 3 such as described above, is likely to allow a pyrolytic product, generated during the heating of the waste, to escape, resulting in foul smells and harmful environmental consequences. The present invention avoids these problems.

Furthermore, since the steam, generated from the heated waste, is collected and removed, the humidity of the returned gas is relatively low, making it much less likely that any remaining steam will cohere to the body of the apparatus and produce undesirable effects with respect to the electric wiring, such as rust or other faults.

Since the temperature of the body of a conventional heater is high, and a harmful substance and gas remain in the heater body immediately after the melting of waste, a long period of time is required to cool the heated waste and thereby solidify and remove the waste from the heater body. By incorporating the hydrodynamic exhaust scrubber 3 of the present invention, many of the harmful substances, generated in the heater body 2 during the heating of the waste, are removed during heating. Furthermore, since the atmosphere in the heater body 2 may be cleaned quickly by using the circulation fan 4 and the scrubber 3, during and subsequent to the heating process, the heated waste is effectively removed from the heater body even if the temperature therein is not as low as in conventional heaters. Since the cooled gas is returned to the heater body 2, both subsequent to and during the operation of the heater, the heater body can be cooled in a relatively short amount of time as compared to conventional apparatus. Accordingly, the disposed waste can be removed from the heater body 2 of the present invention in less time than that for the heater body of a conventional apparatus, thus shortening the disposal cycle to thereby enhance the efficiency of the disposal operation.

Figure 4:
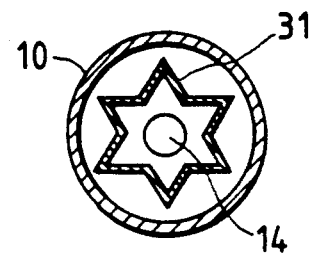
FIG. 4 is a partial sectional view of the scrubber of FIG. 3 along sectional lines A—A.

The present invention is not limited to the above-described embodiment, but may be otherwise constructed as described with reference to FIGS. 3, 4, 5 and 6 as discussed below. For example, the hydrodynamic exhaust scrubber 3 may be replaced by another scrubber 30 shown in FIGS. 3 and 4. The scrubber 30 (FIG. 3) includes a filter 31 provided in the intake space between the partition wall 13 and the water sprinkling member 14. The filter 31, made of a punched plate or a wire net, surrounds an area into which the atomized water is sprinkled from the sprinkling member 14. The cross section of the filter 31 may be shaped in the form of a star, as shown in FIG. 4. The filter 31 may be appropriately closed at upper and lower ends thereof to thereby direct all of the gas through the filter. Since the water contacts the filter 31, and the tar, pyrolytic product and steam pass through the filter, the cooling of the gas and the collection and removal of the tar, product and steam are enhanced.

Figure 5:
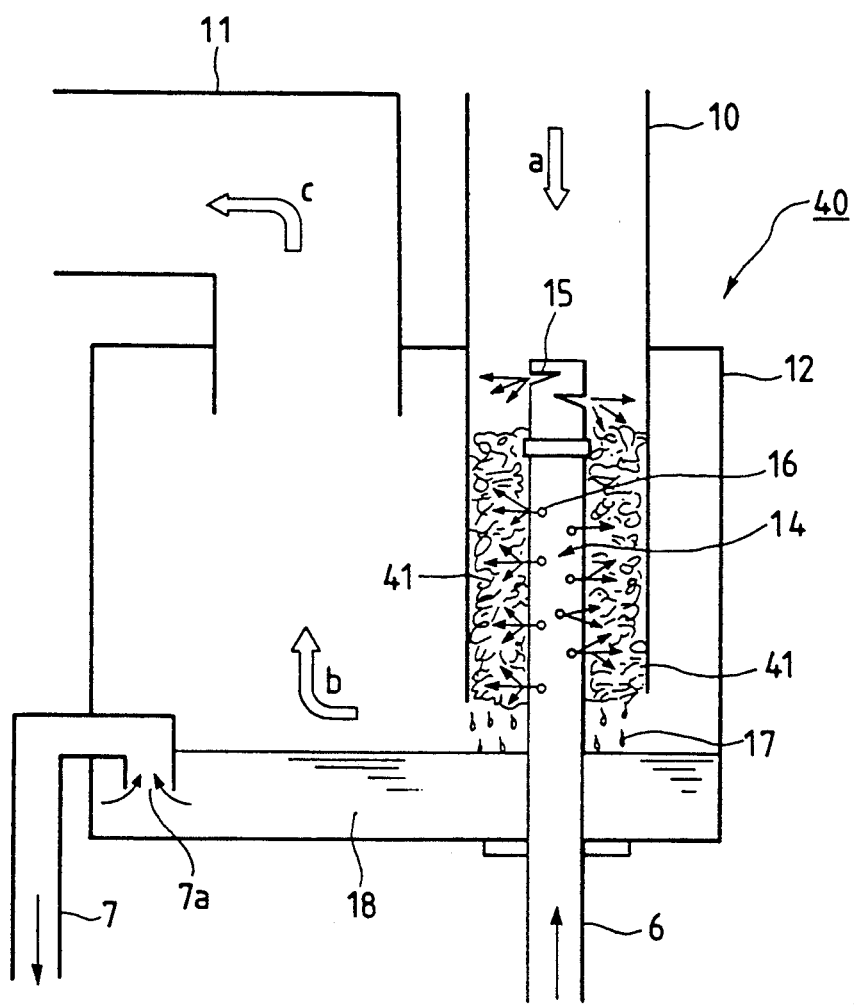
FIG. 5 is a schematic view of another modified hydrodynamic exhaust scrubber of the embodiment shown in FIG. 2
Figure 6:
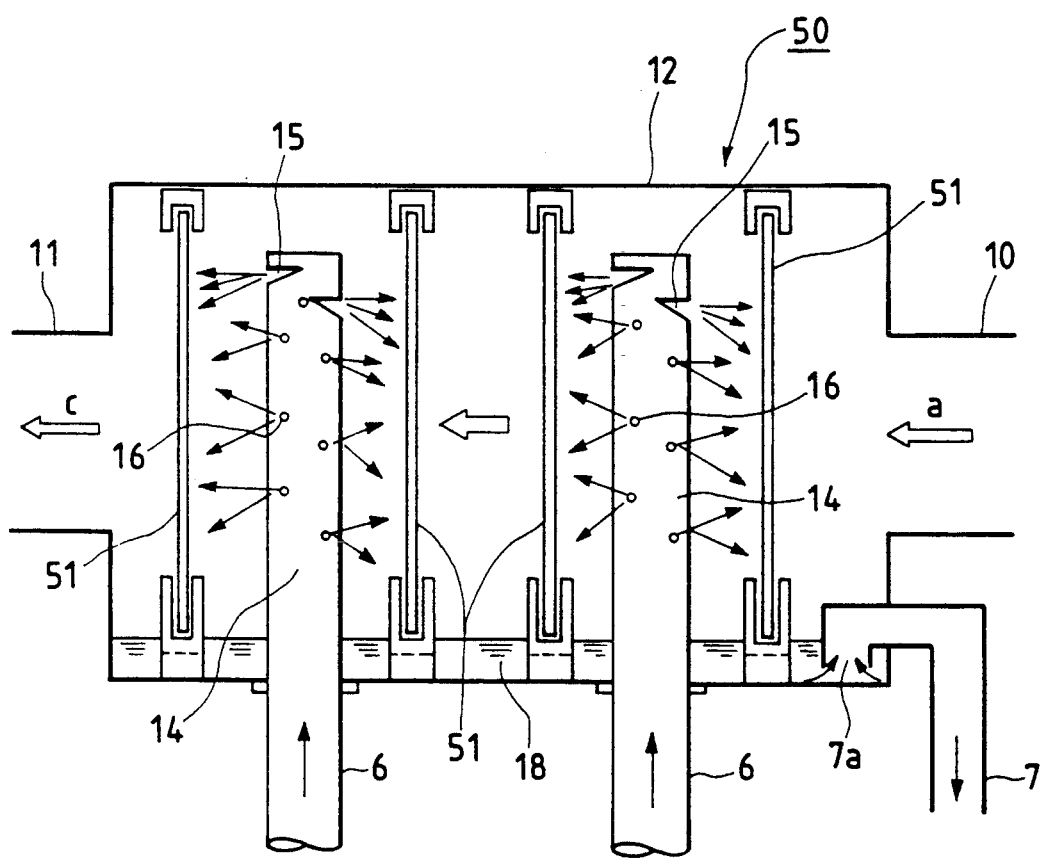
FIG. 6 is a schematic view of yet another modified hydrodynamic exhaust scrubber of the embodiment shown in FIG. 2, including a plurality of water sprinkling members.

The scrubber 3 may also be replaced by yet another apparatus 40 as shown in FIG. 5. The scrubber 40 includes a filter 41 provided between the partition wall 13 and the water sprinkling member 14. The filter 41 is made of densely gathered metal filaments, but is the same, in most other respects, as the filter 31. The scrubber 3 also may be replaced by yet another apparatus 50 as shown in FIG. 6. The scrubber 50 includes filters 51 made of wire nets or punched metal plates dividing the case 12 of the scrubber into a plurality of chambers in which water sprinkling members 14 are provided. The gas, containing the tar, gaseous pyrolytic product and steam, is repeatedly filtered by the filters 51.

In each of the above-described embodiments of the present invention, the atomized water is sprinkled outwardly from the water sprinkling member 14 to the surrounding wall. Of course, the invention may be constructed otherwise such that a water sprinkling member is provided around the intake space for the gas, and atomized water is sprinkled inwardly from the member to the space. Furthermore, each of the water sprinkling members may simply spout the water without thereby atomizing it, the water subsequently being atomized as it strikes the surrounding wall.

In a medical waste disposal apparatus provided in accordance with the present invention, tar, a gaseous pyrolytic product and steam, all of which are generated during the heating of waste, are mixed with water sprinkled in an atomized or spouted state, such that the tar, product and steam are dissolved in, or adsorbed by, the water. The tar, product and steam are thus collected and removed by the apparatus. Since the gaseous pyrolytic product, which may be malodorous and environmentally hazardous, and the steam, which may negatively affect the electric wirings of the apparatus, are both efficiently collected and removed, the waste can be heated without detrimentally affecting the surrounding environment. Since the atmosphere in the body of the heater can be quickly and efficiently cleaned by using a circulation fan and hydrodynamic exhaust scrubber after, as well as during the operation of the heater, the disposed waste can be removed from the heater body even if the temperature therein is not as low as that in the heater body of a conventional disposal apparatus. Since a cooled gas is returned to the heater body, the heater body can be cooled more rapidly than that of the conventional apparatus. As a result, less time is required for removal of the disposed waste, thereby shortening the disposal cycle of the apparatus and enhancing the efficiency thereof.

What is claimed is:

1. A medical waste disposal apparatus for heating medical waste to thereby sterilize said waste, comprising:
   a heater body for heating said waste;
   a hydrodynamic exhaust scrubber including a water sprinkler for sprinkling water in an atomized or spouted state, said water being recovered by said scrubber after said sprinkling;
   forward and backward passages connecting said heater body and said hydrodynamic exhaust scrubber; and
   means for directing a gaseous pyrolytic product and steam, generated during said heating of said waste, through said forward and backward passages, said product being dissolved in said water, said steam being cooled by said water, so as to collect and remove said dissolved product and said steam.

2. A medical waste disposal apparatus according to claim 1, wherein said water sprinkler includes a water sprinkling member extending into a space in said forward passage, said water sprinkling member including sprinkling nozzles in a circumferential portion of said member.

3. A medical waste disposal apparatus according to claim 1, wherein said water sprinkler includes a filter in a water sprinkling area in said forward passage, sprinkled water colliding against said filter while said gaseous pyrolytic product and said steam pass through said filter.

4. A medical waste disposal apparatus according to claim 1, wherein said hydrodynamic exhaust scrubber includes a water drain pipe having a water inlet port which opens toward a bottom of said scrubber.

5. A medical waste disposal apparatus according to claim 1, wherein said scrubber includes a case divided into a plurality of chambers.

6. A medical waste disposal apparatus according to claim 3, wherein said filter in said water sprinkling area has a star-shape.

7. A medical waste disposal apparatus according to claim 3, wherein said filter in said water sprinkling area comprises densely gathered metal filaments.

8. A medical waste disposal apparatus according to claim 3, wherein said filter in said water sprinkling area comprises wire nets.

9. A medical waste disposal apparatus according to claim 3, wherein said filter in said water sprinkling area comprises punched metal plates.

10. A medical waste disposal apparatus according to claim 1, wherein said hydrodynamic exhaust scrubber includes means for recovering the sprinkled water, a gas devoid of the product and the steam being output by said hydrodynamic exhaust scrubber to said heater body.

11. A medical waste disposal apparatus according to claim 1, wherein said water sprinkler includes means for collecting and removing tar, the product and the steam generated from the waste heated by said heater.

12. A medical waste disposal apparatus according to claim 1, wherein said hydrodynamic exhaust scrubber includes means for holding and accumulating a predetermined amount of water, said water preventing a gas having the gaseous pyrolytic product and the steam removed therefrom from exiting from said hydrodynamic exhaust scrubber.

* * * * *